United States Patent [19]

Gallo-Torres

[11] 4,203,967
[45] May 20, 1980

[54] DIAGNOSTIC TEST FOR MALABSORPTION

[75] Inventor: Hugo E. Gallo-Torres, Livingston, N.J.

[73] Assignee: Hoffmann-La Roche Inc., Nutley, N.J.

[21] Appl. No.: 856,818

[22] Filed: Dec. 2, 1977

Related U.S. Application Data

[63] Continuation-in-part of Ser. No. 759,221, Jan. 13, 1977, abandoned.

[51] Int. Cl.$^2$ ............................................ A61K 29/00
[52] U.S. Cl. ................................................ 424/9
[58] Field of Search ........................................ 424/9, 7

[56] References Cited
PUBLICATIONS

*J. Chem. Soc.* (C), 3393 (1971).

*Primary Examiner*—Frederick E. Waddell
*Attorney, Agent, or Firm*—Jon S. Saxe; George M. Gould; R. Hain Swope

[57] ABSTRACT

An improved diagnostic method for detecting malabsorption comprising the oral ingestion by the patient of an effective amount of N-(2-aminoethyl)-glycine (Aeg), collecting the urine for eight hours post ingestion, then detecting the amount of N-(2-aminoethyl)-glycine in the urine by contacting the urine with an indicator substance which indicates the presence of N-(2-aminoethyl)-glycine. Suitable reagents include nihydrin, 2-methoxy-2,4-diphenyl-3-(2H)-furanone, o-phthalaldehyde and fluorescamine, with fluorescamine being preferred. The determination can be made quantitative by treating the urine with a source of active chlorine or bromine prior to contact with the indicator.

9 Claims, No Drawings

DIAGNOSTIC TEST FOR MALABSORPTION

RELATED APPLICATIONS

This application is a continuation-in-part of U.S. Pat. application Ser. No. 759,221 filed Jan. 13, 1977, now abandoned.

BACKGROUND OF THE INVENTION

The need for an accurate, reliable method for testing for malabsorption which is simple enough to be utilized in the clinical situation and sufficiently economical for mass screening has been long felt. The malabsorption syndromes are clinical entities associated with defective absorption of amino acids, sugar, fat, vitamins and minerals. Malabsorption is thus the common denominator in a wide variety of clinical disorders the severity of which covers a broad range and which, when diagnosed, require individual analysis of each patient against the background of the normal process of absorption.

Among the conditions causing malabsorption can be named, for example: celiac sprue (idiopatic sprue in adults and celiac disease in children); Crohn's disease (ileitis, regional enteritis and jejuno ileitis); postsurgical malabsorption (e.g. from total gastrectomy, partial gastrectomy or selective or total vagotomy); short bowel syndrome; bacterial overgrowth of the small bowel (contaminated bowel syndrome); protein-losing gastroenteropathies (a number of abnormal conditions resulting in excessive loss of plasma protein into the gastrointestinal tract with resultant hypoproteinemia); radiation damage to the body (whole body radiation or radiation of the pelvic region); mesenteric artery insufficiency (which may be chronic or related to atherosclerosis); drug-induced malabsorption, particularly the antibiotics, e.g. neomycin, also anticonvulsants, colchicine and diuretics; malabsorption in the aged (mostly amino acids and sugars); tropical sprue, and subclinical malabsorption (tropical enteropathy). Malabsorption is not always accompanied by gross passage of abnormal stools, i.e. steatorrhea, as is incorrectly believed by many lay persons. In fact, unfortunately, most patients with malabsorption do not have steatorrhea and the correct diagnosis is often missed. Further, malabsorption of amino acids usually correlates with malabsorption of carbohydrates and/or fats.

There are a number of methods utilized presently to test for malabsorption. One such series of tests is intake-output balance tests involving fat, radioactive tracers or nitrogens. These tests are difficult to conduct and interpret, e.g. since intestinal motility and nutrient metabolism due to bacteria in the gastrointestinal tract detract from accuracy. The most commonly used screening method for malabsorption in the laboratory is the D-xylose absorption test.

The use of D-xylose as an absorption screening test has several disadvantages. First, the absorption of D-xylose, which occurs predominantly in the duodenum and jejunum, is dependent on a structurally intact small bowel. The absorption of D-xylose is decreased by any condition that alters the absorptive area or capacity of the small intestine. Second, D-xylose is about 60% metabolized. Experiments conducted with D-xylose tagged with $^{14}C$ show substantial quantities of $^{14}C$ incorporated into liver glycogen and also as $CO_2$ in exhaled air.

Further, a considerable and variable amount of D-xylose may not be absorbed from the G.I. tract. The unabsorbed material may produce borborygmi, abdominal cramps and a temporary increase in diarrhea which itself may hinder absorption. Fourth, bacterial overgrowth proximal to the absorptive site may consume enough sugar to produce false low values. Finally, D-xylose is not well standardized due to considerable variance in accepted testing measures. This is, in part, due to the fact that the urine analysis for D-xylose is not specific.

In accordance with the present invention, a screening method for malabsorption is provided which suffers none of the foregoing disadvantageous properties and which facilitates quantitative determinations in the urine.

DETAILED DESCRIPTION OF THE INVENTION

In accordance with the present invention, a method of screening for malabsorption is provided which comprises orally administering to a patient a detectable amount of N-(2-aminoethyl)-glycine, then collecting the patient's urine over the following period of eight hours, and then measuring the N-(2-aminoethyl)-glycine present. N-(2-aminoethyl)-glycine (hereinafter Aeg for purposes of brevity) is a known compound. See, for example, H.D. Law, et al., J. Chem. Soc., (C), 3393 (1971).

Aeg is ideally suited as a malabsorption detection agent since it is almost quantitatively absorbed and is not metabolized. Further, Aeg is relatively non-toxic (L.D.50 in mg/kg of 13,000 per os and >1,000 via intravenous administration). Permeability studies on Aeg indicate that the compound permeates by diffusion and is transported by the ileum, mostly by a diffusion mechanism with little or no active transport.

Experiments conducted with $^{14}C$ labeled Aeg have demonstrated that 30 minutes post oral ingestion only about 0.5% of the administered radioactivity remained in the stomach and this figure decreased to about 0.2% after four hours. The wall of the small intestine contained 18.3, 19.0 and 3.2 percent, respectively, at 30 minutes, 90 minutes and 4 hours. At the same time intervals, the contents of the small intestine contained only 6.5, 4.2 and 1.3 percent, respectively, of the radioactivity. These results clearly establish the rapid uptake and complete absorption of Aeg through the small intestine. Radioactivity in the large intestine was insignificant.

Further studies with labeled Aeg have demonstrated that the only organ to take up significant amounts thereof was the liver which contained 8.5, 15.8 and 18.9 percent, respectively, of the administered radioactivity at 30 minutes, 90 minutes and 4 hours. Amounts taken up by other organs were negligible. Within four hours after oral administration, 75%–85% of Aeg appeared in the urine and, by the tenth hour, it was 99.9%. In practice it has been determined that within eight hours post oral ingestion at least 80% of the administered Aeg should appear in the urine of an individual not afflicted with malabsorption. In most instances, the amount found in the urine should be about 90% or above. It is recommended, therefore, that urine be collected for eight hours in the average clinical use of Aeg. This time period of urine collection represents a further advantage over a similar test with D-xylose wherein it is normally required that urine be collected over a twenty-four hour period.

The determination of the Aeg content of the urine may be carried out by contacting the urine with a substance which indicates the presence of Aeg therein, such as by a color reaction. Although substances and procedures which chemically indicate the presence of Aeg may be utilized, however, procedures utilizing photometric or fluorometric determinations are preferred.

The chemical procedures which can be utilized to detect Aeg include, for example, standard procedures employed in peptide synthesis utilizing reagents such as 1-fluoro-2,4-dinitrobenzene, 1,2-napthoquinone-4-sulfonic acid, 2,4,6-trinitrobenzenesulfonic acid and 5-dimethylaminonaphthalene-1-sulfonyl chloride. In addition, Aeg will, after exposure to chlorine, give a color reaction after spraying with o-tolidine and 4-4-tetramethyldiaminodiphenyl methane, respectively.

More preferred procedures for determining the Aeg content in the urine are colorimetric procedures utilizing photometric apparatus. Examples of suitable procedures are those utilizing reagents such as ninhydrin, 2-methoxy-2,4-diphenyl-3-(2H)-furanone (MDPF) and o-phthalaldehyde. A most preferred procedure in accordance with the present invention utilizes fluorescamine.

The determination of Aeg in the urine utilizing reagents capable of detecting amine-containing compounds in the urine such as those named above, i.e. ninhydrin, MDPF, o-phthalaldehyde and fluorescamine are accurate to an acceptable degree particularly for screening purposes, because, during the test period, Aeg comprises approximately 99% of the compounds in the urine giving a positive indication. Such procedures are therefore satisfactory for screening purposes and as an indication that a quantitative determination may be required.

In order that the determination of Aeg in the urine in accordance with the present invention may be quantitative, it is necessary that a number of potentially interfering amino compounds present in the urine be removed. It has been found in accordance with the present invention that this may be accomplished without affecting the determination of Aeg by treating the urine with a source of active chlorine or bromine. Suitable agents include, for example, chlorine or bromine water, hypochlorus acid, sodium hypochlorite and N-bromoimides and amides, e.g. N-chlorosuccinimide, N-bromoacetamide and the like. Of these, N-chlorosuccinimide is preferred. The treatment with these agents initially chlorinates or brominates then decarboxylates the primary amine of Aeg as well as that of other interfering compounds and converts the secondary amine of Aeg to an imine. To insure that the interfering amino compounds are removed, it is preferred to utilize an excess of said source of active chlorine or bromine. An excess of from about 100 to 1000-fold is preferred. The presence of excess reagent does not interfere with the fluorometric assay.

After treatment with the source of active chlorine or bromine is complete, the sample is then buffered to the optimum pH for the indicator substance being utilized, e.g. between about 9.5 and 10, preferably about 9.7 for fluorescamine, thereby hydrolyzing the Aeg imine to a primary amine.

The primary amine is then treated with the indicator substance and the determination of Aeg made from the resulting color or fluorescence. Wherein fluorescamine is utilized, it reacts efficiently with the primary amine to form highly fluorescent pyrrolinones which have an absorption maximum at 380–410 nm. The fluorescence of the sample is then determined fluorometrically in the manner described in U.S. Pat. No. 3,830,629 issued Aug. 20, 1974 to determine the Aeg content therein. The fluorometric determination can be carried out utilizing a simple, inexpensive instrument such as the Spectronic 20 (Bausch & Lomb), an advantage of the use of fluorescamine over the other reagents specified herein. In addition, fluorescamine is preferred as the indicator substance over the others named herein because it gives a more rapid, substantially more sensitive determination. It is particularly preferable over phthalaldehyde because the chromophore formed by the latter is relatively unstable, therefore requiring all procedures to be carried out promptly.

The method of testing for malabsorption of the subject invention is usable as a single test and is also readily adapted for use in automated analysis of a large number of samples by procedures known in the art, e.g. such as described in the above-mentioned U.S. patent. In either instance, it is contemplated that an average adult would ingest from about 5 grams to about 25 grams of Aeg. The amount to be ingested by children would, of course, be proportionately less. In any event, it is necessary for the patient to have fasted overnight before the test is conducted. It must be borne in mind that the testing method of the subject invention, as is the case with D-xylose, is not specific to a particular type or types of malabsorption and is not intended for such specific diagnosis. The test method described herein, which is particularly useful in large scale screening procedures, is rather to be utilized as a means to alert the clinician that a malabsorption problem is present.

It is contemplated in accordance with the present invention to provide Aeg as a single entity for use in malabsorption screening. It is preferred, however, to provide Aeg in the form of a reagent kit which would provide sufficient reagents for one or a series of tests. Such a kit would preferably contain, in separate containers, Aeg and an indicator compound such as ninhydrin, MDPF, o-phthalaldehyde, fluorescamine or the like, particularly fluorescamine. Wherein a quantitative determination is to be carried out, a source of active chlorine or bromine could also be included as a separate reagent. A buffering agent can optionally be included as a separate reagent.

The following examples further illustrate the invention.

EXAMPLE 1

To study absorption into the portal vein, fasted rats (250 g) were surgically prepared with catheterization of the stomach and the portal vein (Gallo-Torres and Ludorf, Proc. Soc. Exp. Biol. Med. 145: 249-254, 1974). On the day following surgery, samples of portal vein blood were collected every 2.5 minutes for 2 hours after the intragastric infusion of a 0.5 ml saline solution containing Aeg. Similar experiments were conducted using 50 mg cold Aeg or 50 $\mu$C labeled Aeg (Sp. Ac. 1.4 $\mu$Ci/mg).

Absorption balance and tissue distribution studies were carried out in fasted rats, surgically prepared with gastric cannualae. The animals were sacrificed at 30 minutes, 90 minutes or 4 hours after the intragastric administration of 50 mg $^{14}$C-Aeg. Samples of organs and tissues were taken as reported by Gallo-Torres et al., Lipids 6: 318 (1971).

To study urinary excretion either Aeg or $^{14}$C-Aeg was administered, intragastrically, to rats with catheterized bladders. Urine was collected as a function of time for a period of 24 hours. In all cases, metabolism was assessed by detailed amino acid analysis. The results are given in the following tables.

Table I

| Gastric Evacuation and Intestinal Uptake of Aeg | | | |
|---|---|---|---|
| Section of G.I. Tract | Time after I.G. Administration | Percent Radioactivity present | Percent absorbed |
| Stomach | 30 minutes | 0.5 | |
| | 90 minutes | 0.5 | |
| | 4 hours | 0.2 | |
| Small Intestine | 30 minutes | 18.0 (wall) 6.5 (contents) | 72.7 |
| | 90 minutes | 18.0 (wall) 4.2 (contents) | 95.1 |
| | 4 hours | 3.2 (wall) 1.3 (contents) | 98.4 |
| Large Intestine (Plus contents) | 30 minutes | 0.3 | |
| | 90 minutes | 0.2 | |
| | 4 hours | 0.1 | |

The results in Table I clearly demonstrate the rapid uptake and complete absorption of Aeg through the small intestine. Radioactivity in the large intestine was insignificant.

Table II

| Distribution of Aeg in Tissues (Organs) | | | |
|---|---|---|---|
| Tissue | 30 Minutes | 90 Minutes | 4 Hours |
| Brain | <0.1[a] | <0.1 | <0.1 |
| Pituitary Gland | <0.1 | <0.1 | <0.1 |
| Adrenals | <0.1 | <0.1 | <0.1 |
| Ovaries | <0.1 | <0.1 | <0.1 |
| Spleen | <0.1 | <0.1 | <0.1 |
| Heart | <0.1 | <0.1 | <0.1 |
| Uterus | <0.1 | <0.1 | <0.1 |
| Lungs | 0.14 | <0.1 | <0.1 |
| Kidneys | 2.2 | 2.3 | 1.2 |
| Adipose Tissue[b] | 3.3 | 2.8 | 0.7 |
| Blood[c] | 3.9 | 2.7 | 1.7 |
| Muscle[d] | 4.7 | 3.5 | 1.4 |
| Liver | 8.5 | 15.8 | 18.9 |

[a]rounded figures
[b]calculated on 13.6% of body weight attributed to adipose tissue
[c]calculated on 6.0% of body weight
[d]calculated on 40% of body weight The results expressed in Table II show that, except for the liver, Aeg is not deposited to any appreciable extent in the organs and tissues of the animal's body.

EXAMPLE 2

A typical reagent kit or package suitable for the quantitative determination of Aeg in the urine contained the following reagents in powder form in the quantities given. Such a kit could also include a vessel for the collection of urine.

Reagent A: Aeg, 25 g
Reagent B: N-chlorosuccinimide, 5 mg
Reagent C: Fluorescamine, 6 mg In use, the Aeg or some portion thereof as determined by the clinician is dissolved in water with preferably the addition of a small amount of a suitable flavoring agent such as, for example, lemon or pepermint. Following oral ingestion of the Aeg by the patient who had fasted overnight, urine is collected for an eight hour period. Samples of 1 ml are drawn from the pooled urine for testing. The quantities of reagents given above are sufficient for five replicates from a single patient. Each 1 ml sample of urine is added to a suitable test tube containing about 1.5 ml of a 0.2 M sodium citrate buffer, pH 3.25 and the contents mixed well. To this mixture is added 2 ml of a solution of the N-chlorosuccinimide (Reagent B) in 10 ml of 0.05 N hydrochloric acid, the contents mixed and the mixture allowed to stand for one minute. A total of 3.5 ml of a 0.2 M borate buffer (sodium tetraborate decahydrate, pH 9.7) is then added and, after further mixing, 2 ml of a solution of fluorescamine (Reagent C) in 10 ml of acetone is added. The mixture is mixed well for 2 minutes and the fluorescence determined in a spectrophotometer at 350 mm.

EXAMPLE 3

To illustrate a semi-quantitative determination of Aeg in the urine suitable for screening purposes, urine was collected and pooled as described in example 2.

The following solution was prepared. A total of 22.5 ml of 4 M lithium acetate buffer at pH 5.2 was added to 67.5 ml of dimethylsulfoxide. 1.8 Grams of ninhydrin were added to the solution with magnetic bar stirring until dissolved. Nitrogen was bubbled through the solution for 30 minutes. To the solution was then added 0.06 g hydrindantin, thereby reducing the ninhydrin. A 20-fold excess of the thus-formed solution was added to samples of the pooled urine. The samples were heated to 100° C. for 15 minutes, allowed to cool and the purple color read at 570 nm.

EXAMPLE 4

Samples of pooled urine collected as described in example 2 were buffered to a pH of 8.0 with 0.05 M phosphate buffer (0.3 μmol/ml). Two ml samples of the buffered urine were transferred to test tubes. To each test tube was added 0.1 ml of a 0.2 M solution of triethylamine in methanol. The solutions were briefly stirred and 1.9 ml of a 0.01055 M solution of 2-methoxy-2,4-diphenyl-3-(2H)-furanone (MDPF) in methanol added thereto. The amount of MDPF added constitutes from about 20- to 30-fold excess. The samples were mixed for 1 minute in a high speed mixer and allowed to stand for 15 minutes. The absorption intensity of the samples was then determined at 380 nm.

EXAMPLE 5

The following solution was prepared:

A total of 2.5 g boric acid were dissolved in 95 ml deionized water using a magnetic stirrer. The solution was then titrated with a 45% solution of potassium hydroxide to a pH of 10.40±0.02 using a pH meter. To this solution was added 0.3 ml of a 35% by weight solution of an emulsifier, Brij 35 by Pierce Chemical Co., a polyoxyethylene derivative of lauryl alcohol, 0.2 ml of 2-mercaptoethanol and 1 ml of a solution of 65 mg/ml of o-phthalaldehyde in methanol.

In a test tube, a 3 ml sample of pooled urine collected in accordance with example 2 buffered to pH 8 with 0.05 M borate buffer (0.2 μmol/ml) was mixed with 1 ml of the o-phthalaldehyde solution prepared above with stirring for 60 seconds. The solution was immediately transferred to a 1 cm cell and the absorption determined at 335 nm. Immediate transfer and reading were necessary due to the instability of the chromophore formed by mixing the sample and solution.

I claim:

1. A method for testing for malabsorption in a patient comprising:
   (a) orally administering to said patient who had fasted overnight N-(2-aminoethyl)-glycine;
   (b) collecting the urine from said patient during the eight hours following said administration; and
   (c) contacting a sample of the urine with an indicator substance which colorimetrically indicates the presence of N-(2-aminoethyl)-glycine thereby colorimetrically determining the amount of N-(2-aminoethyl)-glycine in the urine.

2. A method in accordance with claim 1 wherein said indicator substance is selected from the group consisting of ninhydrin, 2-methoxy-2,4-diphenyl-3-(2H)-furanone, o-phthalaldehyde and fluorescamine.

3. A method in accordance with claim 2 wherein said indicator substance is ninhydrin.

4. A method in accordance with claim 2 wherein said indicator substance is o-phthalaldehyde.

5. A method in accordance with claim 2 wherein said indicator substance is fluorescamine.

6. A method in accordance with claim 1 wherein said sample of the urine is contacted with a source of active chlorine or bromine before contacting with said indicator substance.

7. A method in accordance with claim 6 wherein said source of active chlorine is N-chlorosuccinimide.

8. A method in accordance with claim 6 wherein said source of bromine is N-bromoacetamide.

9. A method in accordance with claim 1 wherein from about 5 g to about 25 g of N-(2-aminoethyl)-glycine is administered to said patient.

* * * * *